United States Patent [19]

Andersen et al.

[11] 3,988,262

[45] Oct. 26, 1976

[54] METHANATION CATALYST AND PROCESS FOR PREPARING THE CATALYST

[75] Inventors: Kjeld Jorn Andersen, Hillerod; Roberto Candia, Birkerod; Jens Rostrup-Nielsen, Virum, all of Denmark

[73] Assignee: Haldor Topsøe A/S, Soborg, Denmark

[22] Filed: July 2, 1975

[21] Appl. No.: 592,438

[30] Foreign Application Priority Data

July 3, 1974 United Kingdom............... 29418/74

[52] U.S. Cl. ........................ 252/466 J; 260/449 M
[51] Int. Cl.² ..................... B01J 21/06; B01J 23/76
[58] Field of Search ............ 252/466 J; 260/449 M

[56] References Cited

UNITED STATES PATENTS

| | | | |
|---|---|---|---|
| 3,361,535 | 1/1968 | Pollitzer et al. | 260/449 M |
| 3,450,514 | 6/1969 | Sinfelt et al. | 260/449 M |

*Primary Examiner*—W. J. Shine
*Attorney, Agent, or Firm*—Lawrence Rosen; E. Janet Berry

[57] ABSTRACT

The invention concerns a methanation catalyst essentially consisting of nickel on a porous support containing alumina and zirconia in a weight ratio of from 1:2.0 to 1:0.05. This catalyst has good activity at low temperatures and good stability at high temperatures and allows to limit the temperature of the catalyst bed.

7 Claims, No Drawings

METHANATION CATALYST AND PROCESS FOR PREPARING THE CATALYST

This invention relates to a nickel catalyst for preparing gases rich in methane by reacting hydrogen with carbon oxides. Furthermore, the invention relates to a method for preparing such a catalyst and to a process for reacting hydrogen with carbon oxides under formation of methane in the presence of such a catalyst.

Because of the increasing consumption of natural gas there is a great need for improved methods for converting solid and liquid fuels into gases which have calorific values and combustion characteristics similar to those of natural gas. Such methods include gasification of coal and petroleum products followed by a methanation process in which the hydrogen and carbon oxides produced by the gasification are reacted to form methane.

A gas suitable for methanation will contain at least hydrogen and carbon monoxide. It may also contain carbon dioxide and more or less methane and steam. When such gases are contacted with a nickel catalyst at elevated temperature and preferably elevated pressure, the following methanation reactions will occur:

$$CO + 3 H_2 \rightarrow CH_4 + H_2O \quad (1)$$

$$CO_2 + 4 H_2 \rightarrow CH_4 + 2 H_2O \quad (2)$$

The presence of a certain amount of steam in the methanation process has been claimed to be necessary, since otherwise, under certain circumstances, the following undesirable reactions may also occur:

$$2 CO \rightarrow C + CO_2 \quad (3)$$

$$CH_4 \rightarrow C + 2 H_2 \quad (4)$$

The methanation reactiona (1) and (2) are highly exothermic. Consequently, the reactants will heat while passing through the catalyst bed. Too high temperatures at the outlet of the catalyst bed will tend to displace the methanation reactions (1) and (2) towards lower methane concentrations. Furthermore, most nickel catalysts active for the methanation reactions will tend to deactivate at high temperatures. In addition, too high temperatures may increase the tendency for reactions (3) and (4) to occur.

Consequently, it is of importance to limit the maximum temperature of the catalyst bed. For this purpose, the inlet temperature is kept at the lowest value which will still give an acceptable initial reaction rate. Additional measures for avoiding too high temperatures in the catalyst bed include cooling of the catalyst bed or of the reaction gases. Such cooling can take place in various ways. The catalyst can be arranged in two or more separate beds between which the reaction gas is cooled either by indirect heat exchange with cold reaction gas or by direct addition of cold reaction gas. The catalyst bed may also be cooled by circulating a cooling agent through tubes arranged in the catalyst bed or conversely by arranging the catalyst bed in tubes surrounded by a circulating cooling agent. Finally, part of the product gas from the outlet of the methanation reactor may be cooled and recycled to the inlet of the methanation reactor.

It will be understood that a suitable catalyst for methanation processes, among other properties, must have a good activity at low temperatures and a good stability at high temperatures. Among the catalysts previously used for such processes is a nickel catalyst on a support of alumina. Alumina can be prepared in a form having a high specific surface area, thus providing a high activity at low temperatures when impregnated with nickel. On the other hand, such high area aluminas will undergo gradual transformations when heated, which will result in a gradual decrease in surface area. This will particularly occur when large amounts of steam are present. For this reason the temperature range, in which a nickel alumina catalyst will maintain a reasonable good activity, is rather narrow.

We have found a new catalyst composition in which the support material has improved resistance towards transformations under the influence of high temperatures and reacting gases present in methanation processes, while still this new catalyst composition has a good activity at low temperatures. This means that this catalyst composition can operate in a broader temperature range.

Accordingly, we provide a catalyst for methanation reactions consisting essentially of nickel and porous support material containing alumina, the components being evenly distributed amongst each other, in which the content of nickel is from 15 to 40% by weight, calculated as nickel oxide, of the total catalyst and the support material consists of zirconia and alumina in a ratio from 0.05 to 2 parts by weight of zirconia per part by weight of alumina.

Furthermore, we provide a method for preparing by precipitation such a catalyst, which method consists of the sequential steps of (a) preparing an aqueous solution of a nickel salt and containing also compounds of aluminum and zirconium in at least partly dissolved state, (b) precipitating substantially all metal ions from said aqueous solution by the addition of a base, (c) isolating and drying and precipitated metal compounds mixed with any undissolved compounds present in the system formed in step (b), (d) converting the thus-formed mixture of compounds into a mixture of the corresponding oxides by calcination at temperatures between 300° and 500° C, (e) working the thus formed oxides mixture up into particles of any desired shape and size, (f) subjecting the shaped particles to a firing at temperatures between 800° and 1100° C for 2 to 10 hours, and (g) at any desired later moment at least partially reacting the nickel oxide present in the fired particles into metallic nickel.

Still further, we provide a process for reacting hydrogen with carbon oxides under formation of methane in the presence of above catalyst composition.

While the major portion of the catalyst composition in accordance with this invention is composed of the oxides of aluminum, nickel, and zirconium, the composition may further include minor amounts of other compounds deliberately added particularly for improving the mechanical properties of the catalyst. The composition may also include compounds which are inevitably present in the raw materials and which can be tolerated in the final catalyst composition, because they are difficult to remove and have no significant adverse influence on its properties.

The active component of the catalyst composition is metallic nickel formed by reduction of the nickel oxide. The reduction can take place in the methanation reactor by subjecting the catalyst to the reaction gas at elevated temperature. Preferably, however, the catalyst should be separately reduced prior to its loading into the reactor, since in this way optimum conditions for the reduction can be applied. The term "catalyst" will be used herein whether its nickel is present as the metal or as the oxide. For practical reasons, however, the chemical composition of the catalyst will always refer to its oxidized state.

The range of nickel concentration which can be used in the catalyst according to this invention, does not deviate significantly from the range used in hitherto known methanation catalysts. However, in order to obtain a certain minimum activity, the concentration in this catalyst should be at least 5 weight per cent of nickel oxide. On the other hand, the concentration should not exceed about 60 weight per cent, since otherwise the costs of preparing the catalyst may be too high. A concentration in the range of 15 to 40 weight per cent nickel oxide is preferred for most methanation processes, while the range from 25 to 35 weight per cent nickel oxide seems to be an optimum when catalyst activity, catalyst life-time, and catalyst cost are taken into account.

The remaining portion of the catalyst will substantially be the support material comprising alumina and zirconia. The proportion of zirconia to alumina can be varied within the range from 0.05 to 2 weight parts of zirconia per part of alumina. However, the range from 0.1 to 1.0 weight parts of zirconia per part of alumina is preferred and particularly the range of 0.4:1 to 0.7:1 has been found to give a good catalyst stability.

The catalyst is used in the form of discrete particles which may be spheres, rings, cylinders, or they may be of an irregular shape. The particle size may range from 2 to 20 mm dependent upon the operating conditions and design of reactor for which the catalyst will be used. Particularly, considerations with regard to pressure drop through the catalyst bed will determine which particle shape and size should be selected.

The catalyst may be prepared by precipitating compounds of aluminum, nickel, and zirconium from an aqueous solution containing ions of these three metals. The precipitation can be effected by adding to the solution a suitable basic reagent such as for instance ammonia, ammonium carbonate or an alkali metal carbonate or hydroxide added as such or in aqueous solution. Precipitation agents which do not leave any undecomposable substance in the catalyst are preferred, since otherwise the precipitate would have to be carefully washed to remove all traces of for example alkali ions.

Prior to the precipitation, the three metals, aluminum, nickel, and zirconium, may be present in the solution as completely dissolved compounds, i.e. in the form of the corresponding metal ions. However, zirconium and preferably aluminum may be partly present in the form of unsoluble or less soluble compounds finely suspended in the solution. Examples of compounds suitable as raw materials for preparing a catalyst in accordance with the present invention will be given in the following. However, compounds other than those specifically mentioned may also be used.

A suitable aluminum compound is aluminum nitrate, $Al(NO_3)_3 \cdot 9H_2O$. This compound may be used as the only aluminum compound, in which case all aluminum will be present in the solution as aluminum ions. For economic reasons, however, it is preferable that a major portion of the aluminum is present in the form of cheaper aluminum compounds such as for instance alumina hydrate or more or less dehydrated alumina hydrates. These compounds are practically insoluble in water, however, they are suitable when used in combination with a soluble aluminum compound such as the nitrate. The alumina compounds may even preferably be used as the only aluminum compounds if they are first subjected to a treatment in a hot concentrated acid, for instance nitric acid. By such a treatment part of the alumina will dissolve and thereby supply to the solution the desired amount of aluminum ions. Alumina hydrates such as gibbsite and boehmite are particularly suitable for this purpose.

Nickel nitrate, $Ni(NO_3)_2 \cdot 6H_2O$, is a suitable nickel compound which may be used as the only nickel compound, or together with a water insoluble compound as for instance nickel oxide. Preferably, however, nickel nitrate is used alone, since it is available at a reasonable price and in a rather pure form.

A suitable zirconium compound is zirconyl carbonate. This compound may before use be more or less completely dissolved in nitric acid so that zirconium will be present as ions. However, the basic zirconyl carbonate can also be used directly as such, if the solution of aluminum and nickel to which it is added is sufficiently acid to dissolve part of the basic zirconium carbonate under formation of zirconium ions. This will be the case either if the solution contains alumina treated with nitric acid, or if a substantial part of the aluminum and nickel compounds are in the form of nitrates. In both cases sufficient zirconium ions will be formed in the solution. However, it is preferred to dissolve the zirconyl carbonate in nitric acid.

After completion of the precipitation the precipitate is isolated, dried, and calcined under use of conventional operations. There is first a washing either by decantation or filtration. During this washing ions, which during the subsequent drying will form non-decomposable compounds, should be removed as completely as possible. After drying at moderate temperatures aluminum, nickel, and zirconium will be present in the form of oxides, hydroxides, carbonates, or a mixture of these compounds. During a subsequent calcination at 300° to 500° C these compounds are converted into the corresponding oxides. The calcination temperature is selected high enough to convert the carbonates and hydroxides into the corresponding oxides, but not so high that the resulting oxides will undergo a significant sintering.

After a possible grinding, if necessary, the calcined oxides are formed into the desired shape for example by dry pressing or by wet extrusion. In the latter case the catalyst particles will have to be subjected to a drying before a final firing. If the preferred dry pressing technique is used, a few weight per cent of a suitable lubricant such as graphite, stearic acid, or metal stearates are first added to the oxide powder. Further combustible materials such as cellulose powder may also be added to the oxide mixture in order to improve the porosity of the final catalyst. In all cases the catalyst particles after forming are subjected to a firing at temperatures between 800° and 1100° C. The preferred temperature range is from 900° C to 1030° C, and the preferred firing time is from 2 to 10 hours. These firing conditions have been selected to give a satisfactory mechanical strength of the catalyst within a reasonable time and at the same time to avoid a too extensive shrinkage of the catalyst particles which would result in a too low porosity.

The following examples will illustrate how a catalyst composition according to this invention may be prepared. However, the method for preparing the catalyst in accordance with this invention is not strictly limited to the method disclosed in these examples.

EXAMPLE 1

37.7 g nickel nitrate, $Ni(NO_3)_2.6H_2O$, and 112.5 g aluminum nitrate, $Al(NO_3)_3.9H_2O$, were dissolved in 1000 c.c. water heated to 50° C. An aqueous zirconyl carbonate paste having a zirconium content corresponding to 7.7 g zirconium oxide, $ZrO_2$, was suspended in the solution of the nitrates under vigorous stirring during about 10 minutes. Thereafter, 103.2 g of ammonium bicarbonate, $NH_4HCO_3$, was slowly added during 15–30 minutes under continued stirring. The stirring continued for another 2 hours.

The resulting precipitate was filtered and washed with water. After drying for 16 hours at 120° C, the precipitated carbonates of the precipitate were calcined to the corresponding oxides by a calcination at 400° C for 16 hours. The oxide mixture was crushed and passed through a 64 mesh sieve (opening width 0.2mm) The resulting powder was mixed with 3 wt% graphite and 2 wt% cellulose powder and pressed into tablets of 9 mm diameter and 9 mm height. The tablets were fired at 1000° C for 4 hours. The final catalyst, designated as catalyst A, had approximately the following chemical composition: 30 wt% NiO, 46 wt% $Al_2O_3$, and 24 wt% $ZrO_2$.

EXAMPLE 2

51 kg alumina hydrate (75% $Al_2O_3$) in the form of powder was suspended in 2,500 liter water heated to 50° C. 50 liter of 62 wt% nitric acid was added to this suspension under stirring, which continued for 2 hours after the acid was added. 49 kg of an aqueous zirconyl carbonate (47% $ZrO_2$) was then added to the alumina suspension under continued stirring for half an hour. Finally, 113 kg nickel nitrate, $Ni(NO_3)_2.6H_2O$, was dissolved in the suspension under continued stirring for about 1 hour.

To the resulting suspension now containing ions of nickel, aluminum, and zirconium, 136 kg of ammonium bicarbonate, $NH_4HCO_3$, was slowly added for precipitation of carbonates of these metals. To complete the precipitation the suspension was stirred for about 2 hours after addition of the bicarbonate. The precipitate was filtered, washed, and dried at about 120° C to a fine powder which, after calcination for about 10 minutes in a rotating furnace, was mixed with graphite and cellulose powder as in example 1 and pressed into tablets of 4.5 mm diameter and 4.5 mm height. The tablets were then fired at 1000°–1030° C for 3-5 hours. The final catalyst, designated as catalyst B, had approximately the following chemical composition: 32 wt% NiO, 42 wt% $Al_2O_3$, and 26 wt% $ZrO_2$.

EXAMPLE 3

25.5 g of alumina hydrate (75% $Al_2O_3$) was suspended in 3.7 c.c. 62 wt% nitric acid diluted by water to 1200 c.c. The suspension was heated to 50° C and stirred for 2 hours. 24.4 g of an aqueous zirconyl carbonate paste (47% $ZrO_2$) was dissolved in 20.9 c.c. 62 wt% nitric acid. After heating to 50° C the zirconyl solution was added to the alumina suspension together with 56 g nickel nitrate, $Ni(NO_3)_2.6H_2O$. After complete dissolving of the nickel nitrate, carbonates of the metal ions were precipitated by slow addition of 68 g of ammonium bicarbonate, $NH_4HCO_3$.

The precipitate was filtered, washed, dried at 120° C, and calcined at 400° C, as in example 1. After crushing of the dried filter cake to a powder passing through a 64 mesh sieve, 9×9 mm tablets were pressed after addition of 3 wt% graphite and 2 wt% cellulose powder. The tablets were then fired at 1030° C for 3 hours. The final catalyst, designated as catalyst C, had approximately the following chemical composition: 32 wt% NiO, 42 wt% $Al_2O_3$, and 26 wt% $ZrO_2$.

For comparison another catalyst was prepared in the same way as catalyst C was prepared, except that no zirconyl carbonate was added. The resulting final catalyst, designated as catalyst D, had approximately the following chemcial composition: 43 wt% NiO, and 57 wt% $Al_2O_3$.

The resistance of catalyst C and catalyst D to the action of steam at elevated temperature was demonstrated as follows: 10 tablets of each of catalyst C and catalyst D were subjected to an atmosphere of steam and hydrogen in the mol ratio, 10 $H_2O$ to 1 $H_2$ at 800° C during a period of 11 hours. Surface area and axial crushing strength of the tablets were measured after this treatment and compared with corresponding data obtained from tablets which were not subjected to such a steaming. The data are given in the following table I.

Table I

| | B.E.T. Surface Area, m²/g | Axial Crushing Strength, kg/cm² |
|---|---|---|
| Catalyst C: | | |
| Without steaming | 18 | 1610 |
| After steaming | 14 | 1165 |
| Relative Change | 22% | 28% |
| Catalyst D: | | |
| Without steaming | 41 | 294 |
| After steaming | 21 | 143 |
| Relative Change | 49% | 51% |

The data given above in Table 1 demonstrate that catalyst C, which has a composition in accordance with the invention, has a better resistance than a conventional catalyst D without zirconia. For catalyst D both the surface area and the crushing strength were reduced to about half their original values, while for catalyst C they were reduced to only about three quarters of the original values.

The conditions to which these catalysts were subjected are more exacting that the conditions normally used in a methanation process. In this way, the rate of deactivation was increased so that differences in catalyst resistance could be found after a few hours' treatment.

EXAMPLE 4

A catalyst, designated catalyst E, was prepared on an industrial scale under use of the method described in example 3. The amounts of raw materials used in the precipitation were about 4,000 times the amounts used for catalyst C in example 3. After completion of the precipitation, subsequent treatments followed the procedure described in example 2, except that the firing temperature was 990–1020° C. The final catalyst E had approximately the following chemical composition: 32 wt% NiO, 42 wt% $Al_2O_3$, and 26 wt% $ZrO_2$.

The preferred use of the catalyst composition in accordance with this invention is in a process for methanation of gases having a high content of carbon oxides and hydrogen. By subjecting such gases to a methanation process the methane concentration of the product gas may be as high as 80% or even higher, if hydrogen and carbon oxides are present in stoichiometric ratios. Gases suitable for a methanation process may be obtained by gasification of coal or by the water gas process. They may also be obtained by gasification of petroleum products for example by partial oxidation of fuel oils or by steam reforming of hydrocarbons such as naphtha. Such processes will provide gases in which the ratio between hydrogen and carbon oxides is suitable for an almost complete conversion to methane in a subsequent methanation process. In this way solid and liquid fuels can be converted to a gas having a calorific value and other combustion characteristics similar to those of natural gas. Such as gas can, therefore, be used to supplement natural gas in periods, where the consumption of natural gas exceeds the production.

The following three examples, examples 5, 6, and 7, will illustrate how a methanation process was conducted on a pilot plant scale under use of a catalyst having a composition in accordance with this invention, and having been prepared in accordance with this invention.

EXAMPLE 5

Catalyst E prepared as described in example 4 was used in a methanation experiment after having been pre-reduced at 800° C, so that substantially all nickel was present in the catalyst as free nickel.

The methanation experiment was conducted for 30 hours in a pilot plant simulating the conditions of an adiabatic reactor of industrial size operated with recycle. For this purpose, the pilot plant was equipped with a tubular reactor of a heat and pressure resistant alloy having an inner diameter of 50 mm and a total length of 2.8 m. In this reactor 3.9 liter of catalyst E was arranged in a bed having a height of 2.05 m. To compensate for loss of heat to the surroundings the reactor was supplied with electrical elements.

A feed gas consisting of about 25 vol% carbon monoxide and 75 vol% hydrogen was preheated to about 300° C and pressed through the catalyst bed together with part of the product gas which was recycled at a rate of about 5 times the feed gas rate. The temperature of the recycle stream was also adjusted to about 300° C at the reactor inlet. A certain amount of steam preheated to about 300° C was added to the feed and recycle streams, so that the combined gas stream at the inlet consisted of carbon monoxide, hydrogen, methane, and steam. Further operating details are given in Table II.

EXAMPLE 6

Another methanation experiment was conducted for 30 hours in the same pilot plant and with the same amount of pre-reduced catalyst E as used in example 5, except that there was no recycle of product gas.

A feed gas composition simulating a gas prepared by a process of steam reforming naphtha at rather low temperature was used for this experiment. The approximate composition was as follows: 0 vol% CO, 16 vol% $H_2$, 60 vol% $CH_4$, and 23 vol% $CO_2$.

Further operating data from this experiment are given in tabel II. It is seen that there are still unreacted hydrogen and carbon dioxide present in the product gas. This is due to the relatively high steam rate used in these experiments. Under such circumstances complete reaction cannot be obtained for thermodynamic reasons.

EXAMPLE 7

A third methanation experiment was conducted in the same pilot plant for several thousand hours to demonstrate the stability of the catalyst at operating conditions. A slightly less amount of pre-reduced catalyst E than that used in examples 5 and 6 was used in this experiment. As in example 5 there was a recycle of product gas. Further operating data are given in Tabel II. The conditions used here are typical conditions for the first step in a two-step methanation procedure.

The temperatures through the catalyst bed are given after various periods of operation. From the explanations given herin it will be understood that most of the methanation reactions occur in the part of the catalyst bed in which there is a temperature increase. From the temperatures given in tabel II it is seen that at 105 hours of operation the reactions are completed at a distance of 30 cm from the inlet. At 541 hours the reactions are almost completed at 40 cm, while at 2097 hours the reactions are almost completed at 50 cm. These changes prove that the active zone of the catalyst bed, in which the methanation occurs, is gradually moving forward through the catalyst bed, so that a catalyst section, which initially is operated at the high outlet temperature, will have to operate at gradually decreasing temperatures, until eventually it will operate at the low inlet temperature.

This example 7 demonstrates the stability of the catalyst of this invention. Even after several thousand hours' operation, the methanation reactions are substantially completed in the first third of the total catalyst bed.

Table II

| Example No. | 5 | 6 | 7 | | |
| --- | --- | --- | --- | --- | --- |
| Catalyst bed | | | | | |
| Volume, c.c. | 3,900 | 3,900 | 3,300 | | |
| Height, cm | 205 | 205 | 173 | | |
| Total Hours on Stream | 30 | 30 | 2,400 | | |
| Operating Pressure, kg/cm² g | 35 | 23 | 30 | | |
| Temperatures, °C | | | | | |
| At hours on stream | 30 | 30 | 105 | 541 | 2097 |
| Distance from inlet: | | | | | |
| 0 cm | 290 | 271 | 298 | 301 | 298 |
| 10 cm | 328 | 298 | 371 | 387 | 337 |
| 20 cm | 406 | 307 | 511 | 484 | 411 |
| 30 cm | 455 | 316 | 600 | 570 | 500 |
| 40 cm | 460 | 321 | 600 | 595 | 573 |
| 50 cm | 461 | 324 | 600 | 600 | 596 |
| outlet | 460 | 327 | 600 | 600 | 600 |

Table II-continued

| Example No. | | 5 | 6 | 7 |
|---|---|---|---|---|
| Feed Gas Rate (dry), Nm³/h | | 10.18 | 4.34 | 14.40 |
| Recycle Gas Rate (dry), Nm³/h | | 47.49 | 0.00 | 24.00 |
| Steam Rate, kg/h | | 2.40 | 3.00 | 10.00 |
| Gas Composition (dry), vol % | | | | |
| Feed Gas | CO | 25.0 | 0.0 | 23.9 |
| | $H_2$ | 75.0 | 16.0 | 74.6 |
| | $CH_4$ | 0.0 | 61.0 | 0.6 |
| | $CO_2$ | 0.0 | 23.0 | 0.9 |
| Inlet Gas | CO | 4.3 | 0.02 | 9.8 |
| | $H_2$ | 24.2 | 15.6 | 48.6 |
| | $CH_4$ | 71.5 | 61.4 | 36.8 |
| | $CO_2$ | 0.02 | 23.0 | 4.8 |
| Gas at 25 cm | CO | 0.6 | 0.04 | — |
| | $H_2$ | 15.8 | 5.2 | — |
| | $CH_4$ | 83.4 | 71.3 | — |
| | $CO_2$ | 0.2 | 23.5 | — |
| Outlet Gas | CO | 0.02 | 0.03 | 2.0 |
| | $H_2$ | 13.7 | 2.8 | 34.0 |
| | $CH_4$ | 86.2 | 76.5 | 57.0 |
| | $CO_2$ | 0.04 | 20.7 | 7.0 |

What is claimed is:

1. A catalyst for methanation reactions consisting essentially of nickel and a porous material containing alumina and zirconia, the components being evenly distributed amongst each other, wherein the content of nickel is from 15 to 40% by weight, calculated as nickel oxide, of the total catalyst and zirconia and alumina are present in a ratio of from 0.05 to 2.0 parts by weight of zirconia per part by weight of alumina and which catalyst has been prepared by the sequential steps of (a) preparing an aqueous solution of a nickel salt and containing, in at least partly dissolved state, aluminum and zirconium compounds thermally decomposable to the oxides, (b) precipitating substantially all metal ions from said aqueous solution by the addition of a base, (c) isolating and drying the precipitated metal compounds mixed with any undissolved compounds present in the system formed in step (b), (d) converting the thus-formed mixture of compounds into a mixture of the corresponding oxides by calcination at temperatures between 300° and 500° C., (e) working up the thus-formed oxides mixture into particles of any desired shape and size, (f) subjecting and shaped particles to a firing temperature of between 800° and 1100° C. for two to ten hours and (g) subsequently at least partially reducing the nickel oxide present in the fired particles into metallic nickel.

2. A catalyst as claimed in claim 1, in which the content of nickel is from 25 to 35% by weight, calculated as nickel oxide, of the total catalyst, the ratio of zirconia to alumina being from 0.1 to 1.0 part by weight of zirconia per part by weight of alumina.

3. A catalyst as claimed in claim 1, in which the ratio of zirconia to alumina is from 0.4 to 0.7 part by weight of zirconia per part by weight of alumina.

4. A method for preparing a methanation catalyst, said catalyst consisting essentially of nickel and a porous material containing alumina and zirconia, the components being evenly distributed amongst each other, wherein the content of nickel is from 15 to 40% by weight, calculated as nickel oxide, of the total catalyst and zirconia and alumina are present in a ratio of from 0.05 to 2.0 parts by weight of zirconia per part by weight of alumina; consisting essentially of the following sequential steps: (a) preparing an aqueous solution of nickel salt and containing, in at least partly dissolved state, aluminum and zirconium compounds thermally decomposable to the oxides, (b) precipitating substantially all metal ions from said aqueous solution by the addition of a base, (c) isolating and drying the precipitated metal compounds mixed with any undissolved compounds present in the system formed in step (b), (d) converting the thus-formed mixture of compounds into a mixture of the corresponding oxides by calcination at temperatures between 300° and 500° C., (e) working up the thus-formed oxides mixture into particles of any desired shape and size, (f) subjecting the shaped particles to a firing temperature of between 800° and 1100° C. for two to ten hours and (g) subsequently at least partially reducing the nickel oxide present in the fired particles into metallic nickel.

5. A method as claimed in claim 4, in which the aqueous solution of step (a) is prepared by (i) treating an alumina hydrate with an aqueous solution of nitric acid to form a suspension of an alumina compound also present in partly dissolved state, (ii) adding to said suspension zirconyl carbonate which dissolves by the reaction with the nitric acid present in the system, and (iii) dissolving nickel nitrate in the resulting suspension.

6. A method as claimed in claim 4, in which the base added in step (b) is selected from the group consisting of aqueous ammonia, aqueous ammonium carbonate and aqueous alkali metal carbonates and alkali metal hydroxides.

7. A method as claimed in claim 4, in which the firing temperature is between 900° and 1030° C.

* * * * *